US005723720A

United States Patent [19]
Brede et al.

[11] Patent Number: 5,723,720
[45] Date of Patent: Mar. 3, 1998

[54] PROCESS FOR THE DEVELOPMENT OF ENDOPHYTE-INFECTED PLANTS

[75] Inventors: A. Douglas Brede, Veradale; Suichang Sun, Liberty Lake, both of Wash.

[73] Assignee: J. R. Simplot Company, Boise, Id.

[21] Appl. No.: 483,897

[22] Filed: Jun. 7, 1995

[51] Int. Cl.$^6$ ............... A01H 4/00; A01H 17/00; A01H 5/00; A01G 13/00
[52] U.S. Cl. ............... 800/200; 800/250; 800/DIG. 8; 800/DIG. 55; 435/223; 435/240.48; 435/240.49; 47/58; 47/DIG. 1
[58] Field of Search ............... 800/200, 250, 800/DIG. 8, DIG. 55; 435/223, 240.48, 240.49; 47/58, DIG. 1

[56] References Cited

U.S. PATENT DOCUMENTS

| | | |
|---|---|---|
| 4,940,834 | 7/1990 | Hurley et al. |
| 5,443,981 | 8/1995 | Belanger et al. ............... 435/223 |
| 5,549,729 | 8/1996 | Yamashita ............... 71/26 |

OTHER PUBLICATIONS

J.F. Kearney et al., "Infection of Somatic Embryos to Tall Fescue with *Acremonium coenophialum*", Crop Science 31 (1991) pp. 979–984.

S.L. Clement et al., "Acremonium Endophytes in Germplasms of Major Grasses and Their Utilization for Insect Resistance", *Biotechnology of Endophytic Fungi of Grasses*, C.W. Bacon et al., eds., (1994) pp. 185–199.

L. Lee et al., "Molecular Manipulation of Grasses", Abstract for Proceedings of the 32nd Grass Breeders Work Planning Conference, Aug. 16–18, 1992.

C.R. Funk et al., "Importance of Acremonium endophytes in turf–grass breeding and management", *Agric. Ecosystems Environ.*, 44 (1993) pp. 215–232.

C.R. Funk et al., "Role of Endophytes in Enhancing the Performance of Grasses Used for Conservation and Turf", IPM for Turfgrasses and Ornamentals, A.L. Leslie et al. eds. (1989) pp. 203–210.

C.R. Funk et al., "Role of Endophytes in Grasses Used for Turf and Soil Conservation", Biotechnology of Endophytic Fungi of Grasses, C.W. Bacon et al. eds. (1994) pp. 201–209.

J.F. White et al., "Endophyte–Host Associations in Grasses. XVI. Patterns of Endophyte Distribution in Species of the Tribe Agrostideae", *American Journal of Botany* 79 (1992) pp. 472–477.

M.L. Fraser et al., "The Role of Endophytes in Integrated Pest Management for Turf", Handbook of Integrated Pest Management for Turf and Ornamentals, A.R. Leslie ed., CRC Press Inc. (1994) pp. 521–528.

M.C. Johnson et al., "Infection of Tall Fescue with *Acremonium coenphialum* by Means of Callus Culture", *Plant Disease* 70 (1986) pp. 380–382.

B.D. O'Sullivan et al., "Infection of Plantlets, Derived from Ryegrass and Tall Fescue Meristems, with Acremonium Endophytes", *Proceedings of the Second International Symposium on Acremonium/Grass Interactions*, D.E. Hume et al. eds., (1993) pp. 16–17.

M.P. Rolston, "Use of Endophyte in Plant Breeding and The Commercial Release of New Endophyte–Grass Associations", *Proceedings of the Second International Symposium on Acremonium/grass Interactions: Plenary Papers*, D.E. Hume et al. eds. (1993) pp. 171–173.

*Primary Examiner*—Douglas W. Robinson
*Assistant Examiner*—Melissa Kimball
*Attorney, Agent, or Firm*—Rothwell, Figg, Ernst & Kurz

[57] ABSTRACT

Beneficial endophytes which live within certain plants are known to provide desirable, cost-effective biological insect control. Many naturally occurring grasses host symbiotic endophytic fungi. However, beneficial endophytes have never been found in several species of turf grass, including species of bentgrasses and Kentucky bluegrasses, two commercially important turf grasses which are used extensively on golf courses and for lawn turfs. The invention of this application relates to new methods of inoculating plant tissues which allow the development of endophyte-enhanced varieties of turfgrasses, and to the turf grass varieties produced using the methods.

31 Claims, No Drawings

PROCESS FOR THE DEVELOPMENT OF ENDOPHYTE-INFECTED PLANTS

This invention relates to new cultivars of bentgrass and Kentucky bluegrass which are stably infected with performance-enhancing endophytes and to methods of developing these cultivars. The cultivars provide new turf grass varieties having increased resistance to damage by insect pests and certain fungal infections and increased tolerance to environmental stress such as summer heat and drought conditions.

BACKGROUND

Endophytes of the genus Acremonium are beneficial fungi which live within their plant hosts. They exist within the plant for all or nearly all of their life cycle. Endophytes are found within the leaves, stems and flowering parts of healthy plants, generally lack a sexual stage in their development, and have limited, if any, pathogenic effects on their plant hosts. Plant biologists have been aware of the presence of endophytes in many natural grasses for more than 100 years. However, they have only recently begun to appreciate the role that these fungi play in enhancing the performance of certain grasses, including those that are useful for conservation of natural landscapes and for turf on lawns.

The role and importance of fungal endophytes in the persistence and performance of grasses was first recognized by plant biologists in the 1980s. The association of an endophytic fungus, *Acremonium lolii*, with resistance to insects, which can cause extensive damage to perennial ryegrasses and other grasses used for pasture, turf and conservation, was reported by Prestidge and coworkers in 1982. Subsequent work by others demonstrated that the persistence and performance of the perennial ryegrasses used for turf in many parts of New Zealand was due to endophyte-enhanced resistance to the Argentine stem weevil *Listonotus bonariensis*.

Since these earlier studies first suggested an association between infection with an endophytic fungus and increased resistance to insects, researchers have demonstrated the increased resistance of endophyte-infected grasses to sod webworms, billbugs, chinch bugs, some aphid species, and armyworms. Endophytic fungi have also been observed to deter certain root-feeding pests under laboratory conditions and have been reported to be associated with decreased populations of nematodes on the roots of infected fescues. (M. L. Fraser and J. P. Breen, "The Role of Endophytes in Integrated Pest Management for Turf," in *Handbook of Integrated Pest Management for Turf and Ornamentals*, A. R. Leslie, ed., 1994, CRC Press Inc., Boca Raton, Fla., pp 521–528.)

It is now generally recognized that many of the improved turf-type perennial ryegrasses developed in the United States, prior to the discovery of endophyte associated insect resistance, are infected with higher levels of the endophyte Acremonium. Additionally, many of the attractive persistent ryegrasses, which have been propagated from "old turfs", are infected with an Acremonium endophyte.

As plant breeders have become increasingly aware of the benefits of infection with Acremonium endophytes, they have attempted to develop methods to incorporate the fungus into elite cultivars of grasses, including turf grasses. The predominate methods used have been modifications of conventional breeding methods, such as backcrossing and recurrent selection. These techniques have been moderately successful when used with grasses that are known to be naturally infected with endophytes such as tall fescue, perennial ryegrass and some species of fine fescue, probably due to the fact that Acremonium endophytes are maternally transmitted and that most of these turfgrasses are largely cross-pollinated.

U.S. Pat. No. 4,940,834 discloses a method for developing a new variety of perennial ryegrass in which a selected, naturally occurring maternal seed parent, which hosts an endophytic fungus capable of enhancing its host plant's characteristics, is crossed with a paternal pollen parent plant of the same or different variety as the maternal parent. Progeny from that cross, which display the desired endophyte associated characteristics, are selected for propagation by any of the methods of plant propagation presently used by those of skill in the art of plant breeding. These methods include paired hybridization, polycross hybridization and recurrent selection. In paired hybridization an endophyte-containing plant, acting as a female, is crossed with a non-endophytic plant acting as a male, contributing pollen to the cross. In polycross hybridization an endophyte-containing female is pollinated with pollen from several contributing males at the same time. In recurrent selection the seed from an endophyte-containing female is harvested, individually planted, grown, and re-harvested, and the vegetative characteristics of the next generation are evaluated. Unfortunately, these types of breeding methods are only useful for developing endophyte-containing cultivars of plant species that are naturally infected with endophytes.

The introduction of endophytes into callus tissue derived from endophyte-free tall fescue has been described by Johnson and coworkers. (Johnson, Bush, and Siegel, "Infection of Tall Fescue with *Acremonium coenophialum* by Means of Callus Culture," *Plant Disease* 70 (1986) pp 380–382.) Explants of young soft tissue were taken as the panicles were beginning to emerge from the flag leaf and were cultured in Murashige and Skoog medium supplemented with 2,4-dichlorophenoxy acetic acid (2,4-D). Small pieces of this tissue were inoculated with endophyte, isolated from the periphery of a fungal colony. Methods for developing new grass varieties involving tissue culture of callus tissue and regeneration of plantlets from this tissue are generally not successful, since they are difficult to carry out on the scale needed to generate sufficient plants to allow for selection of rare infection events. Successful inoculations have only been achieved in plant species which are naturally infected with endophyte fungi.

It presently appears that endophytes do not naturally occur in certain plant species, particularly in popular turf grasses such as the bentgrasses of the genus Agrostis and Kentucky bluegrasses of the genus Poa. A recent field survey by White et al. (*American Journal of Botany* 79 (1992) 472–477) found endophytes in only four species of the thirteen species of Agrostis collected from populations in New Jersey and Alabama. No endophyte-infected samples from these populations were found for the bentgrass species *A. altissima, A. arachnoides, A. borealis, A. canian, A. exarata, A. ghiesbreghtii, A. palustris, A. stolonifera*, or *A. tenuis*. Recent surveys of "old turf" populations of Agrostis plants in England by the present inventors failed to identify any specimens of endophyte-infected bentgrass. Additionally, there have been no reports of samples of endophyte-infected Kentucky bluegrasses.

Plant biologists have attempted to develop methods for directly incorporating endophytes into grass cultivars, so that the performance-enhancing characteristics resulting from natural endophyte infection can be introduced into desirable, elite turf grasses such as bentgrass and Kentucky bluegrass. These approaches have involved attempts to inoculate seedlings with endophytes directly, as well as, attempts to introduce endophytes into callus grown in tissue culture, into somatic embryos isolated from callus tissue and into plantlets developed in tissue culture from meristems. Heretofore, there have been no reports of the successful introduction of beneficial endophytes into cultivars of bentgrass or Kentucky bluegrass.

SUMMARY OF THE INVENTION

The present invention provides new cultivars of bentgrasses and Kentucky bluegrass that are stably infected with beneficial fungal endophytes. These cultivars have certain enhanced performance characteristics, including improved resistance to insects, resistance to diseases and tolerance to stress, which result in improved grass growth and survival under unfavorable environmental conditions such as summer heat and drought.

The amount of turf management needed to maintain healthy grass plants throughout the growing season is reduced for new varieties of endophyte-infected turf grasses developed from these stably infected cultivars. Fewer applications of chemical insecticides are needed to maintain a healthy turf. Moreover, because insect damage to the grasses is reduced, there is less opportunity for the invasion of weeds into the turf so that the need for treatments with herbicides is also reduced.

This invention further provides methods for infecting turf grasses with endophytes by direct inoculation. The methods can be used to develop new endophyte-infected turf grasses having desirable characteristics, including improved resistance to insects, growth characteristics and tolerance to environmental stress.

DETAILED DESCRIPTION OF THE INVENTION

The novel endophyte-infected turf grass cultivars of this invention may be established initially by methods which involve directly incorporating endophytes into seedlings or other appropriate plant tissues of naturally occurring endophyte-free grasses. Once the plant tissues are infected, they are used for the development of novel turf grass cultivars having endophyte-enhanced performance characteristics. These novel cultivars are then used in more traditional plant-breeding procedures for producing further improved grass varieties. Turf grasses which are not naturally infected by endophytes include those species known as bentgrass, of the genus Agrostis, particularly creeping bentgrass of the species *Agrostis stolonifera*, which is understood to be synonymous with *Agrostis palustris* and Kentucky bluegrass, of the genus Poa, particularly the species *Poa pratensis*, which is understood to be synonymous with *Poa angustifolia*, both of which are used in intensively managed turf surfaces such as lawns and golf course greens, tees and fairways.

In a second aspect of this invention, novel endophyte infected turf grass may be developed by an elective crossing procedure. Varieties of closely related grasses which are naturally infected with endophyte may selected in the wild as native, uncultivated grasses. The species may include "wild" varieties of native bentgrasses. These species may further include "wild" Poa species such as *Poa arida, Poa nervosa, Poa sterilis, Poa glaucifolia, Poa cuspidata, Poa arctica, Poa ampla* as well as other wild species of Poa. The inventors of the present application have identified a number of such endophyte-infected species of Poa which are related to Kentucky bluegrass, *Poa pratensis*, and which have a similar morphology and appearance. Surprisingly, it has now been found that endophytes can be introduced into Kentucky bluegrass by crossing with these selected wild-type species.

While not wishing to be bound by theory as to why the methods of this invention are successful, the present inventors have postulated that a wild-type bluegrass with a rhizome habit might have a closer genetic and physical compatibility with Kentucky bluegrass and may therefore be a host for endophytes which would be more compatible with Kentucky bluegrass, which is also a rhizome habit species. Heretofore, it was not known that these species could be crossed with Kentucky bluegrass, much less that the progeny would be stably infected with endophytes. Furthermore, prior to the investigation of the present inventors, it had never before been confirmed that the Poa species *P. arida, P. nervosa, P. sterilis, P. glaucifolia* and *P. arctica* were in fact infected with endophyte.

Endophyte-infected plants of wild-type Poa are brought into the greenhouse and propagated, then hybridized with cultivars of Kentucky bluegrass, the infected wild-type plants being used as the maternal parents. Endophyte-infected segregating progeny of this hybridization having dominate characteristics of Kentucky bluegrass are selected for further propagation.

Selected grass varieties can be infected with Acremonium endophytes as seedlings, as callus tissue, as plantlets derived from single meristems or as somatic embryos, using methods known to those of skill in the art of plant tissue culture. Methods of culturing plant tissues are well known to modern plant biologists. See for example, Johnson, Bush, and Siegel, "Infection of Tall Fescue with *Acremonium coenophialum* by Means of Callus Culture," *Plant Disease* 70(1986) pp 380–382. These authors describe a method of culturing the peduncle tissue of endophyte-free tall fescue (*Festuca arundinacea*) plants in tissue culture, using Murashige and Skoog medium supplemented with 2,4dichlorophenoxy acetic acid (2,4-D). Explants were derived from the soft young tissue when the panicles were beginning to emerge from the flag leaf.

Plantlets for inoculation can be prepared from single meristems of mature bentgrass or Kentucky bluegrass plants using procedures analogous to those described for perennial ryegrass plants by O'Sullivan and Latch using grass meristems in tissue culture. (B. D. O'Sullivan and G. C. M. Latch, "Infection of plantlets derived from ryegrass and tall fescue meristems, with *Acremonium endophytes*," in *Proceedings of the Second International Symposium on Acremonium/Grass Interactions*, D. E. Hume, G. C. M. Latch and H. S. Easton, eds. (1993) AgResearch, Grassland Research Center, Private Bag 11008, Palmerston North, New Zealand.)

Preferably, endophyte inoculations are carried out on grass seedlings. The use of seedlings is advantageous, because it allows the inoculation and screening of large numbers of individual plants, and therefore increases the chances of identifying endophyte-infected plants in inoculations where the efficiency of infection is low. Infection of a single endophyte-free species or variety may require the inoculation of between 100 to 5000 seedlings. Preferably, between 1000 to 2000 seedlings are inoculated.

Specimens of native bentgrass ecotypes can be collected from plant populations in Europe and its neighboring islands, western Asia, and parts of the Middle East. Introduced populations can be found throughout all temperate regions of the world, including North America, where the grasses have escaped from cultivation. The species can be identified by trained botanists or agriculturalists by the characteristic shape of the leaf blade, and the arrangement of the seed panicle at maturity. Alternatively, known, commercially available, endophyte-free turf grass varieties may be used in these methods. Preferred, commercially available, endophyte-free turf grass varieties which may be used for developing the cultivars of the present invention include the creeping bentgrass varieties known as Putter, Southshore, Providence, SR1020, Pennlinks, Penncross, Penneagle, Emerald, Pro/cup, Crenshaw, Cato, 18th Green, and Cobra. Preferred bluegrass varieties include those known as Adelphi, Amazon, Cheri, cheri, classic Eclipse, Freedom, Glade, Julia, Limousine, Nustar, Ram I, and Nublue. Additional preferred bluegrass varieties include those known as Dawn, Destiny, Fylking, Huntsville, Liberty, Merion, Nassau, Nugget, Suffolk, Wabash, A-34, Able I, Classic, Monopoly, Shamrock, Merit, Barblue, Touchdown, Indigo, Blacksburg, Abbey, Coventry, Washington, Georgetown, Preakness, Livingston, P-104, P-105, 1757, Challenger, Midnight, Unique, Apex, Pennpro, SR2000, SR2100, Trenton, Opal, Gnome, Haga, and common.

Seeds to be used for the germination of seedlings are collected from any of the bentgrass or Kentucky bluegrass, particularly the varieties disclosed above. Seeds from commercial varieties of bentgrass and Kentucky bluegrass can be obtained directly from commercial sources.

Endophytes useful for infecting bentgrass seedlings are isolated from natural endophyte-infected grasses collected from nature in areas where the Agrostis genus is native and well adapted. Collecting endophytes from the epicenter of a species' origin provides the collector with plant specimens having increased genetic diversity. In theory, this occurs because the plants at the epicenter have had a longer time to evolve and are therefore more diverse. Additionally, the occurrence of endophyte-infected plants can also be expected to increase in number as one nears the species' epicenter, since the endophyte-host interaction is highly specific.

Compatible endophytes are identified only through methods of inoculation and subsequent microscopic examination. To date, there have been no tests developed by plant scientists to predict whether a given endophyte genotype will be compatible with a given grass genotype. Selection of a large number of possible endophyte candidates, and a large number of grass candidates greatly increases the possibility of a compatible match. Prior to the studies disclosed herein, plant biologists have been unable to find a satisfactory "match" between an isolated endophyte and a grass genotype for the bentgrass and Kentucky bluegrass species.

Collected native grasses and commercial grasses can be surveyed for endophytes by employing the culm examination technique. Culms, the jointed stem of the grass, are split longitudinally and the inner tissues stained with 0.5% rose bengal, then scraped onto a clean glass slide and examined microscopically. Similar procedures are used for screening inoculated seedling and plantlets grown from tissue culture to ascertain whether inoculation procedures have produced endophyte-infected specimens.

Endophytes may be isolated from infected tissues of collected grasses by procedures known in the art. For example, see J. F. White et al., *American Journal of Botany* 79 (1992) at 473. The surfaces of culms or leaf sheaths are preferably disinfected, e.g., by treating with a solution of 20% hypochlorite bleach solution, then rinsing in sterile water. The disinfected plant tissues are then plated on an appropriate medium such as potato dextrose agar (PDA).

Certain endophyte strains are known to cause a plant disease known as choke, which effectively kills the developing grass seedhead, preventing seed production on those plants. These strains of endophyte are not suitable for use for commercial seed-propagated cultivars and should therefore be avoided when selecting strains of endophytes for inoculation. Likewise endophyte-infected wild-type grasses displaying the symptoms of choke should be avoided for use in selective hybridizations.

Plant tissues may be inoculated with endophytes by placing the endophyte into a direct wound or cut made in the plant tissue. Where the plant tissues to be inoculated are plantlets from germinated seedlings or developed from plant meristems, the cut may be made directly into the stem of the plant. The inoculation is carried out by placing a small piece of an endophyte directly on or into the cut. Likewise callus tissue may be cut and the endophyte mycelium applied directly to the wound. One preferred method, which can be used on plant parts other than seed, utilizes the above-ground grass stolon, centering on the secondary shoot arising from the node as the tissue for carrying out the inoculations.

To improve the chances that endophyte enters the plant tissue, the inoculation with endophyte mycelium should be repeated from 1 up to 5 times, at approximately 7 to 10 day intervals after the previous inoculation has been done. The repeated inoculation procedure is essential to successful incorporation of the endophyte, because it provides a greater opportunity for the endophyte to penetrate the host before the host wound heals.

Inoculated plant tissues are allowed to heal, and the tissues are allowed to develop into plants which can be further cultivated by methods appropriate for the tissue type initially inoculated. If plantlets have been inoculated, they are grown in sterile culture for six to eight weeks before they are transferred to greenhouse and transplanted into soil.

If callus tissue has been inoculated with endophyte, the tissue is transferred into auxin-free medium to allow the development of somatic embryos and plantlets.

Inoculated plants are removed from the sterile growth medium using forceps and transferred into (non-sterile) greenhouse potting mixture. The plantlets are grown in potting mix for 4 to 6 weeks until they are of sufficient size that a piece of the stem material can be excised and checked under the microscope for the presence of the endophyte.

Having established endophyte-infected cultivars of bentgrass and Kentucky bluegrass, new infected cultivars can advantageously be established by conventional plant-breeding techniques. The endophyte infection is maternally transmitted to progeny. Therefore, by crossing an infected maternal parent with a variety having desirable agronomic characteristics genetically diverse, commercially useful varieties of endophyte-infected bentgrass and Kentucky bluegrass can be created. By providing endophyte-infected lines of these previously uninfected species, the present invention enables the preparation of a wide variety of infected cultivars by crossing with any other plant that is capable of breeding with an infected plant. Accordingly, the present invention provides a wide variety of endophyte-infected bentgrass and Kentucky bluegrass cultivars, whereas before this invention, infected plants of these species were unknown. The invention is further illustrated by the following examples, which are not intended to be limiting.

EXAMPLE 1

Preparation of Endophyte-Infected Creeping Bentgrass Varieties

Creeping bentgrass seeds were sterilized by a process known as double sterilization. The seeds were first washed with a solution of 50% hypochlorite bleach, then rinsed with distilled water three to four times. The seeds were drained and allowed to rest overnight. The entire sterilization process was repeated the next day so that any spores which germinated overnight were also destroyed.

The sterile seeds were transferred to a sterile Murashige and Skoog medium without plant hormones, and then allowed to grow until they were between 0.5 and 1.0 inches in length, which usually required between 7 to 10 days of growth.

Clones from the bentgrass variety Putter were inoculated with mycelium taken from a culture of endophyte identified as AS-7, which was obtained from Dr. James White of Auburn University. The endophyte was originally isolated from plants growing in central England, the exact species of which has not been ascertained. The seedlings were inoculated by making a small cut with a sterile scalpel into the stem of the plant, then laying an endophyte directly on top of, or into the cut. The process was repeated after 7 to 10 days when the wound began to heal. The process could be repeated additional times at 7 to 10 day intervals to increase the probability of successful inoculation. The inoculation with endophyte mycelium is done immediately after each incision is made.

Inoculated seedlings were allowed to grow in petri dishes with sterile Murashige and Skoog medium for six to eight weeks after the inoculations. They were then moved to the greenhouse and transplanted into soil to allow the new plants to develop. Samples of tissue from the young plants were examined microscopically to determine if the endophyte had established itself in the cuttings after the plants have developed four or five tillers.

After the endophyte has been confirmed within the plant, and reverified after 4 to 6 months of vegetative growth, then the infected plant is placed into a conventional plant breeding program. After inoculation, the plant line is usually too restricted or narrow in genetic base to constitute a complete and finished variety. Its genetics are broadened by crossing the infected female with pollen from one or more male pollen-contributing plants. Seed is then harvested from only the female, since the endophyte fungus is not carried through the pollen grains in the reverse direction. Each subsequent generation of cultivar development is similar, in that the seed is harvested exclusively from the endophyte-containing female; the pollen-contributing males are not harvested.

In the final step of varietal development, seed is harvested from a population of endophyte-containing plants in a breeder seed field. Each plant in the population has been checked under the microscope to confirm the presence of endophyte prior to anthesis. Any non-endophyte plants are discarded following pollination, and their seed is not harvested. In theory, this produces a variety with near 100% endophyte infection.

For the later generations of Foundation, Registered, and Certified seed, seed is planted and harvested in a conventional manner. Breeder seed is sown to produce Foundation, Foundation seed is sown to produce Registered, and Registered seed is sown to produce Certified. With each generation, the level of endophyte in the population is monitored by selecting a random collection of seed and examining them in the laboratory. Fields with unsatisfactory endophyte infection are rejected when the level of endophyte-infected plants falls below levels at which the benefits attributable to endophyte are no longer seen.

Bentgrass cultivars developed by the foregoing methods posses certain desirable performance characteristics, in addition to the presence of an endophyte. These cultivars have medium dark green genetic color, an upright leaf orientation, lack of steminess when grown as maintained turf, and good tolerance to close mowing, disease, drought, and stress. These cultivars also exhibit improved botanical insect resistance, in addition to the resistance provided by the endophyte.

EXAMPLE 2

Preparation of Endophyte-Infected Kentucky Bluegrass Varieties

Introduction of an endophyte into Kentucky bluegrass was achieved using a selective hybridization procedure. The "wild" Poa species *Poa glacifolia* and *Poa arctica* were collected from native grass populations located in eastern Montana. The specimens were potted and brought into the greenhouse prior to seedhead expression, at which time their infection with endophyte was reverified. These species are related to *Poa pratensis*, Kentucky bluegrass, in that they have a rhizome habit and a similar morphology and appearance.

To carry out the selective hybridization endophyte-infected native plants in pots were placed in a crossing block arrangement and pots containing Kentucky bluegrass varieties were placed around the infected plants. The Kentucky bluegrass varieties used included Glade, Limousine, NuBlue, Eclipse, Midnight and Apex. These plants were obtained from field plantings, and the plants themselves were nearing flowering at the time of the procedure. Care was taken to choose Kentucky bluegrass plants that matched in coincidence of flowering, or anthesis, with the wild endophyte-infected species. This was accomplished by either moving the plants outside, where it was cooler, to slow down flowering, or by moving them inside the heated greenhouse to speed up flowering.

After anthesis took place, which occurred after approximately 20 to 26 days, water was withheld from the plants to provide stress to stimulate the maturation of seed. Seed were removed from the endophyte-infected plants, and then planted in greenhouse potting mix to initiate germination. The germinating seedlings were transferred to 2×2 inch cells in greenhouse flats and were grown until they began producing lateral tillers. At this time plants with morphological characteristics resembling Kentucky bluegrass were selected, and plants resembling the maternal wild-type plant were discarded. Hybrid progeny having Kentucky bluegrass morphology constituted from about 1% to about 30% of the total plants obtained from the selective hybridization procedure, depending on the mother plant used.

The status of viable endophyte in the hybrid plants was confirmed by microscopic examination, and noninfected plants were discarded. Infected plants were transplanted to field nurseries for further testing and evaluation, and seed was harvested from plants showing characteristics similar to Kentucky bluegrass.

Segregating progeny showing characteristics of Kentucky bluegrass were identified and propagated in outdoor nurseries for further selection. Progeny with strictly maternal appearance were discarded. The presence of endophyte in the selected progeny was confirmed by microscopic examination prior to transplanting.

Traditional plant breeding methods were used to stabilize the plant line and broaden it into a plant cultivar following identification of infected interspecific hybrids. These cultivars possess certain performance characteristics, in addition to those provided by the presence of endophyte, including a medium dark green genetic color, a moderately high turf density, rapid ground coverage and spring greenup, and good tolerance to close mowing, disease, drought and stress. They also contain improved botanical insect resistance.

We claim:

1. A cultivar of a non-naturally occurring turf grass comprising a naturally endophyte-free grass, selected from the group consisting of bentgrass of the genus Agrostis and Kentucky bluegrass of the genus Poa, infected with an Acremonium endophytic fungus.

2. The cultivar of claim 1 wherein the naturally endophyte-free grass is a bentgrass.

3. The cultivar of claim 2 wherein the bentgrass is selected from the group consisting of the species *Agrostis altissima, Agrostis arachnoides, Agrostis borealis, Agrostis canian, Agrostis exarata, Agrostis ghiesbreghtii, Agrostis palustris, Agrostis stolonifera and Agrostis tenuis.*

4. The cultivar of claim 2 wherein the bentgrass is a creeping bentgrass of the species *Agrostis stolonifera.*

5. The cultivar of claim 4 wherein the bentgrass is designated by the varietal name Putter.

6. The cultivar of claim 1 wherein the naturally endophyte-free grass is a Kentucky bluegrass.

7. The cultivar of claim 6 wherein the naturally endophyte-free grass is a Kentucky bluegrass of the species *Poa pratensis.*

8. The cultivar of claim 7 wherein the naturally endophyte-free grass is a Kentucky bluegrass selected from the varieties of Adelphi, Amazon, Cheri, Classic, Eclipse, Freedom, Glade, Julia, Limousine, Nustar, Ram I, Nublue, Dawn, Destiny, Fylking, Huntsville, Liberty, Merion, Nassau, Nugget, Suffolk, and Wabash.

9. Seed of the cultivar of claim 1.

10. A non-naturally occurring turf grass comprising an endophyte-infected bentgrass developed from the cultivar of claim 2.

11. A non-naturally occurring turf grass comprises an endophyte-infected Kentucky bluegrass developed from the cultivar of claim 6.

12. A method for developing a turf grass cultivar comprising inoculating a turf grass, selected from the group consisting of a bentgrass and a Kentucky bluegrass, with an Acremonium endophyte.

13. The method of claim 12 wherein the turf grass is a bentgrass.

14. The method of claim 13 wherein the turf grass is selected from the group consisting of the species *Agrostis altissima, A. arachnoides, A. borealis, A. canian, A. exarata, A. ghiesbreghtii, A. palustris, A. stolonifera and A. tenuis.*

15. The method of claim 13 wherein the turf grass is the creeping bentgrass *Agrostis stolonifera.*

16. The method of claim 15 wherein the turf grass is the creeping bentgrass of the varietal known as Putter.

17. The method of claim 12 wherein the turf grass is a Kentucky bluegrass.

18. The method of claim 17 wherein the turf grass is a Kentucky bluegrass of the species *Poa pratensis.*

19. The method of claim 17 where the turf grass is a Kentucky bluegrass selected from the varieties of Adelphi, Amazon, Cheri, Classic, Eclipse, Freedom, Glade, Julia, Limousine, Nustar, Ram I, Nublue, Dawn, Destiny, Fylking, Huntsville, Liberty, Merion, Nassau, Nugget, Suffolk, and Wabash.

20. The method of claim 12 wherein the turf grass plant inoculated is a seedling.

21. The method of claim 12 where the turf grass plant inoculated is a somatic embryo from a callus growing in tissue culture.

22. The method of claim 12 where the turf grass plant inoculated is a callus tissue.

23. The method of claim 12 where the turf grass plant inoculated is plantlet developed in culture.

24. A method of infecting a turf grass with an endophyte comprising inoculating a grass seedling, selected from the group consisting of bentgrass seedlings and Kentucky bluegrass seedlings, wherein said seedling is cut, an endophyte is placed on top of the cut, and endophyte-infected adult turf grass cultivars are established from the infected seedlings.

25. The method of claim 24 wherein the turf grass is a creeping bentgrass.

26. The method of claim 25 wherein the turf grass is a creeping bentgrass of the species *Agrostis stolonifera.*

27. The method of claim 25 wherein the turf grass is the creeping bentgrass varietal Putter.

28. The method of claim 24 wherein the turf grass is a Kentucky bluegrass.

29. A method of infecting a creeping bentgrass of the variety Putter with an Acremonium endophyte comprising inoculating a bentgrass seedling by cutting the plant material, placing the endophyte on top of the cut, and establishing endophyte-infected cultivars from endophyte-infected seedlings.

30. Seed of a bentgrass cultivar wherein the cultivar is prepared by the method of claim 13.

31. Seed of a Kentucky bluegrass cultivar wherein the cultivar is prepared by the method of claim 17.

* * * * *